US00PP25126P3

(12) United States Plant Patent
Olesen

(10) Patent No.: US PP25,126 P3
(45) Date of Patent: Dec. 2, 2014

(54) FLORIBUNDA ROSE PLANT NAMED 'POULPAL038'

(50) Latin Name: *Rosa*
Varietal Denomination: Poulpal038

(75) Inventor: Mogens Nyegaard Olesen, Fredensborg (DK)

(73) Assignee: Poulsen Roser A/S, Fredensbore (DK)

( * ) Notice: Subject to any disclaimer, the term of this patent is extended or adjusted under 35 U.S.C. 154(b) by 205 days.

(21) Appl. No.: 13/507,017

(22) Filed: May 31, 2012

(65) Prior Publication Data

US 2013/0326759 P1 Dec. 5, 2013

(51) Int. Cl.
*A01H 5/00* (2006.01)

(52) U.S. Cl.
USPC ..... Plt./144

(58) Field of Classification Search
CPC ..... A01H 5/0222; A01H 5/00; A01H 5/02
USPC ..... Plt./144, 124, 133, 103
See application file for complete search history.

(56) References Cited

PUBLICATIONS

Poulsen Roser A/S. List of variety production 2009/2010, retrieved on Feb. 19, 2014, retrieved from the Internet at <http://florpak.pl/pl/download/Roze_prezentacja_Poulsen_sadzonki.pdf> 16 pp. plus p. 15 Google translation, total 17pp.*
Mai. Rose Propagation for Home Gardeners, revised 2008, pp. 1-43.*
Google translation of p. 15 for Poulsen Roser A/S, List of Variety Production 2009/2010, one page.*

* cited by examiner

*Primary Examiner* — June Hwu

(57) ABSTRACT

A new garden rose plant of the Compact Floribunda class which has abundant, white flowers and attractive foliage. This new and distinct variety has shown to be uniform and stable in the resulting generations from asexual propagation.

1 Drawing Sheet

Botanical designation: *Rosa* hybrid.
Variety denomination: 'Poulpal038 '.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2004 and the resulting seeds were planted in a controlled environment in Fredensborg, Denmark. The new variety, named 'Poulpal038', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant white flowers;
2. Vigorous, but compact growth when propagated both as a budded rose and on its own roots; and
3. Exceptional disease resistance.

This combination of qualities is not present in previously available commercial cultivars of this type, known to the inventor, and distinguish 'Poulpal038' from all other varieties of which we are aware.

As part of the rose development program, Mogens N. Olesen germinated the seeds from the aforementioned hybridization during winter of 2004 and conducted evaluations on the resulting seedlings in a controlled environment in Fredensborg, Denmark. 'Poulpal038' was selected in the spring of 2005 by the inventor as a single plant from the progeny of the aforementioned hybridization.

Asexual reproduction of 'Poulpal038' by traditional budding and rooted cuttings was first done by Mogens N. Olesen in the nursery in Fredensborg, Denmark in July, 2005. This initial and other subsequent asexual propagations conducted in controlled environments have demonstrated that the characteristics of 'Poulpal038' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpal038'. Specifically illustrated in the drawing are flowers at various stages of development, flower in parts, leaves, and stems. Illustrated plants are 2 years of age.

DETAILED DESCRIPTION OF THE VARIETY

The following is a description of 'Poulpal038', as observed in its growth in in a field nursery in Bakersfield, Calif. 2 years of age, and were grown on their own roots. Color references are made using The Royal Horticultural Society (London, England) Colour Chart, 2001, except where common terms of color are used.

For a comparison, several physical characteristics of the rose variety 'Poulgret', U.S. Plant Pat. No. 10,729 are compared to 'Poulpal038' in Chart 1.

CHART 1

| | 'Poulpal038' | 'Poulgret' |
|---|---|---|
| Petal Count | 26 | 25-28 |
| Flower Diameter | 60-80 mm | 50-60 mm |
| General Tonality of Flower Color | White Group 155B | White Group 155B |

FLOWER AND FLOWER BUD

Blooming habit: Continuous.

Flower bud:

*Size*.—Upon opening, 25 mm in length from base of receptacle to end of bud. Bud diameter is 12 mm.

*Bud form*.—Ovoid.

*Bud color*.—As sepals divide petals are White Group 155B.

*Sepal inner surface*.—Color: Green Group 138B. Surface: Smooth.

*Sepal outer surface*.—Color: Yellow-Green Group 144A. Texture: Smooth with weak pubescence.

*Sepal shape*.—Apex: Cirrhose. Base: Flat at union with receptacle.

*Sepal margin*.—Margins have weak foliaceous appendages on three of the five sepals.

*Sepal size*.—25 mm long by 7 mm wide.

*Receptacle*.—Texture: Smooth. Size: 7 mm in height by 6 mm wide. Color: Yellow-Green Group 144A. Shape: Campanulate.

*Pedicel*.—Surface: Smooth. Length: 30 to 40 mm. Diameter: 2 mm on average. Color: Yellow-Green Group 144A. Strength: Moderate.

*Peduncle*.—Length: 3 to 7 cm. Diameter: 3 mm. Color: Yellow-Green Group 144A. Surface texture: Smooth.

Flower bud development: Flower buds are borne in clusters of 3 to 5 flower buds per stem.

Flower bloom:

*Fragrance*.—Moderate honey perfume.

*Duration*.—The blooms have a duration on the plant of approximately 14 days. Petals fall cleanly away from plant after flowers have fully matured.

*Size*.—Flower diameter is 60 to 80 mm when open. Flower depth is 30 mm.

*Flower shape*.—General shape is high centered, with a high pointed center which is tightly closed.

*Shape of flower, side view*.—The upper portion is flat. The lower portion is concave.

Petalage: Under normal conditions, flowers have 26 petals total, 3 to 4 of which are petaloids.

General tonality of flower: Open flowers are White Group 155B.

Petal color, upon opening and after opening:

*Outer petals*.—Upper surface: White Group 155B. Lower surface: White Group 155B.

*Inner petals*.—Upper surface: White Group 155B with intonations of Yellow Group 8D at the middle zone. Lower surface: White Group 155B with intonations of Yellow Group 8D at the middle zone.

*Basal petal spots*.—Upper surface: Yellow Group 3C. Lower surface: Yellow Group 3C.

Petals:

*Petal reflex*.—Strong.

*Margin*.—Entire and uniform. No undulations of margin observed.

*Shape*.—Generally rounded. Apex shape: Rounded. Base shape: Acute.

*Size*.—35 mm (l)×35 mm (w).

*Texture*.—Smooth.

*Thickness*.—Average.

Petaloids:

*Size*.—8 mm (l) by 4 mm (w).

*Quantity*.—3 to 4.

*Shape*.—Asymmetric, round at apex, acute at base.

*Color*.—White Group 155B with intonations of Yellow Group 8D at the middle zone and marginal zone. Petal spot of Yellow Group 3C.

Reproductive organs:

*Pollen*.—None observed.

*Anthers*.—Size: 2 mm in length. Color: Yellow Group 12B. Quantity: 85 on average.

*Filaments*.—Color: Yellow Group 12A. Length: 7 mm.

*Pistils*.—Length: 7 mm. Quantity: 47 on average.

*Stigmas*.—Color: Greyed-Yellow Group 162D.

*Styles*.—Color: Red Group 43C.

*Location of stigmas*.—Level in location relative to the length of the filaments and the height of the anthers.

*Hips*.—None Observed.

PLANT

Plant growth: Upright and bushy. Plants are 40 cm in height, and 40 cm wide.

Stems:

*Color*.—Juvenile growth: Yellow-Green Group 144B. Mature growth: Yellow-Green Group 144A.

*Length*.—On average, canes are 30 cm from the base of the plant to the flowering portion.

*Diameter*.—4 mm.

*Internodes*.—On mature canes, there is an average distance of 40 mm between nodes.

*Surface texture*.—Young wood: Smooth. Older wood: Smooth.

Long prickles:

*Incidence*.—10 prickles per 10 cm of stem.

*Size*.—Average length of prickles on mature stems is 6 mm.

*Shape*.—Upper portion is linear. Lower portion is concave.

*Color*.—Juvenile prickles: Greyed-Yellow Group 162C. Mature prickles: Greyed-Yellow Group 162C.

Plant foliage:

*Compound leaf*.—90 mm (l)×70 (w).

*Quantity*.—2 leaves per 10 cm of stem on average.

*Leaf bearing angle to the stem*.—90 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: About 8 mm in length. Quantity: 2 per compound leaf. Shape: Linear, slightly broad based with outward extending apices. Margins: Finely serrated. Color: Yellow-Green Group 144A.

*Petiole*.—Length: About 20 mm. Diameter: 2 mm. Surface Texture: Smooth.

*Upper surface*.—Color: Yellow-Green Group 144A.

*Lower surface*.—Color: Yellow-Green Group 144B.

*Rachis*.—Length: About 40 mm. Surface Texture: Smooth. Upper surface: Color: Yellow-Green Group 144A.

*Lower surface*.—Color: Yellow-Green Group 144B.

*Leaflet*.—Quantity: Normal number of leaflets leaves in middle of the stem is 5 leaflets. Margins: Serrated. Size: Average size of the terminal leaflet on normal leaves is 40 mm in length by 30 mm wide. Shape: Generally ovate. Base: Rounded. Apex: Mucronate. Texture: Smooth at upper and lower surface. Thickness: Average. Arrangement: Odd pinnate. Venation: Reticulate. Glossiness: Very glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Compact Floribunda rose class named 'Poulpal038', substantially as illustrated and described herein, due to its abundant white flowers, disease resistance, and extended period of bloom.

* * * * *

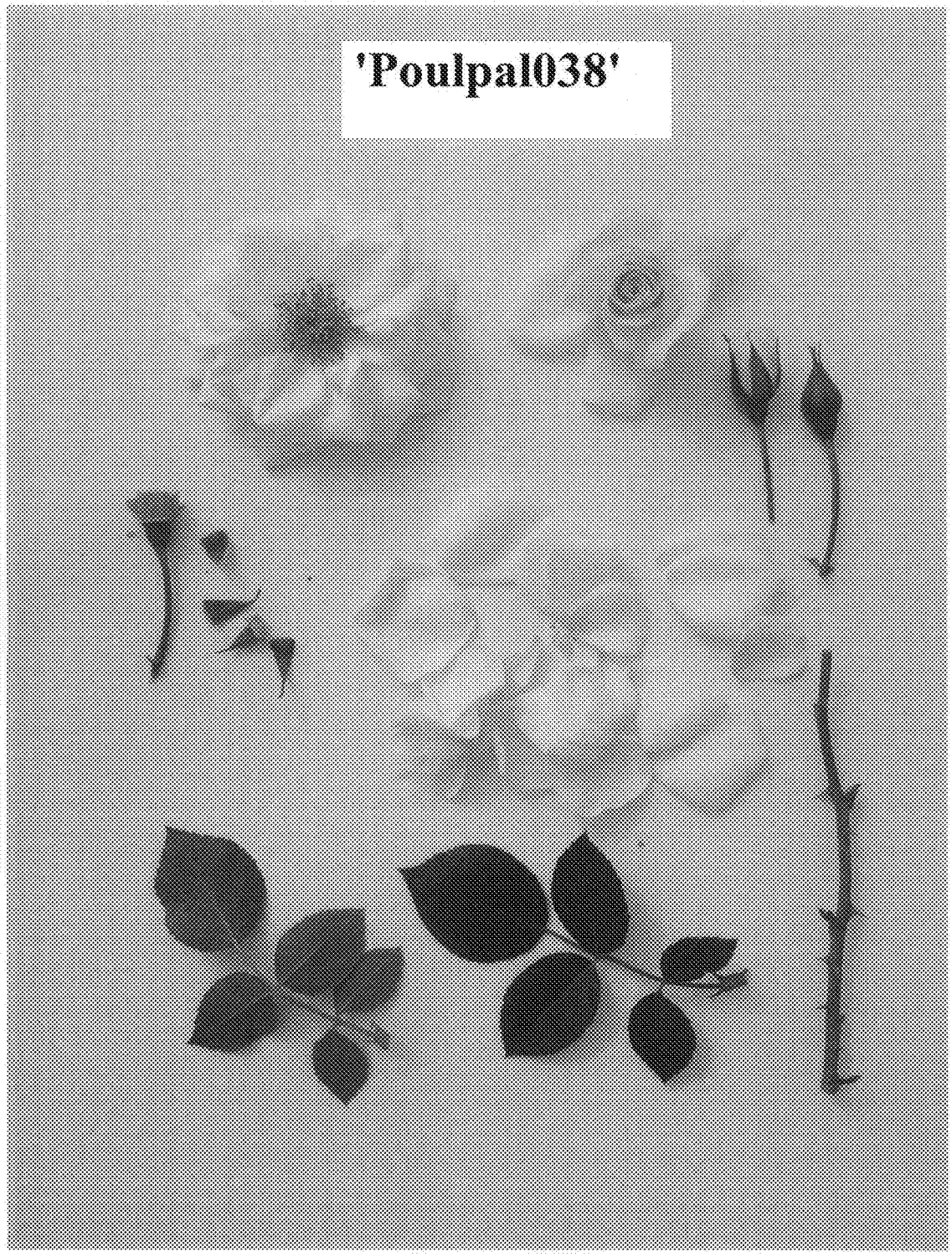
'Poulpal038'